(12) United States Patent
Fasano

(10) Patent No.: US 6,586,018 B1
(45) Date of Patent: Jul. 1, 2003

(54) HERBAL COMPOSITION

(76) Inventor: Sabina Fasano, 1306 Perico Point Cir., Bradenton, FL (US) 34209

(*) Notice: Subject to any disclaimer, the term of this patent is extended or adjusted under 35 U.S.C. 154(b) by 0 days.

(21) Appl. No.: 09/945,323

(22) Filed: Aug. 31, 2001

(51) Int. Cl.⁷ .......................... A01N 65/00; A61K 35/78
(52) U.S. Cl. ................... 424/746; 424/732; 424/734; 424/757; 424/760; 424/765
(58) Field of Search ................................ 424/746, 732, 424/734, 757, 760, 765

(56) References Cited

U.S. PATENT DOCUMENTS

| | | | |
|---|---|---|---|
| 4,592,912 A | | 6/1986 | Nickolaus |
| 4,689,230 A | | 8/1987 | Ayoub |
| 5,565,199 A | | 10/1996 | Page et al. |
| 5,569,459 A | | 10/1996 | Shylankevich |
| 5,707,630 A | | 1/1998 | Morrow |
| 5,855,892 A | * | 1/1999 | Potter et al. ................. 514/456 |
| 5,952,374 A | * | 9/1999 | Clarkson, Jr. et al. ...... 514/456 |
| 6,238,707 B1 | | 5/2001 | Chun |
| 6,346,267 B1 | * | 2/2002 | Fry et al. ..................... 424/451 |
| 6,391,309 B1 | * | 5/2002 | Empie et al. ................ 514/783 |

OTHER PUBLICATIONS

Article entitled "Herbal Therapies for Perimenopausal and Menopausal Complaints", Debra Israel PHD, and Ellis Quinn Youngkin, P.h.D., R.N.C., Pharmocotherapy 1997; 17(5); 970–984.
Commission E Monographs, Licorice root, pp. 161–162, Sep. 21, 1991.
Commission E Monographs, Ginger root, pp. 135–136 Sep. 9, 1990.
Commission E. Monographs, Damianaleaf and herb, pp. 325–326, Mar. 2, 1989.
Commission E. Monographs, Paprika, p. 178, Feb. 1, 1990.
"A Principle In Raspberry Leaves Which Relaxes Uterine Muscle", J.H. Burn and E.R. Withell, THE LANCET, Jul. 5, 1941.
American Botanical council, HERBCLIP, article entitled Red Clover Isoflavones Reduce Cardiovascular Risk to Reduced Arterial Elasticity in Menopausal Women, Oct. 15, 1999.
Article entitled "Biological effects of isoflavones in young women: importance of the chemical composition of soyabean products", A Cassidy, S. Bingham and K. Setchell, Br. J. Nutr. 1995 Oct; 74(4): 587–60.
Article entitled Soy protein and isoflavones: their effects on blood lipids and bone density in postmenopausal women, S.M. Potter, J.A. Baum, H. Teng, R. J. Stillman, N. F. Shay, J.W. Erdman, Jr., Am. J. Nutr. 1998 Dec.; 68 (6 Suppl): 1375S–1379S.
Article entitled"Effects of Extracts from *Cimi cifuga racemosa* on Gonadotroping Release in Menopausal women and Ovariectomized Rats", Eva–Maria Duker et. al., pp. 420–424, Planta Med. 57 (1991).
Article entitled "Therapeutic Efficacy and Safety of *Cimicifuga racemosa* for Gynecologic Disorder", Advances in Natural therapy, vol. 15 No. 1, Jan./Feb. 1998, Eckehard Liske, PhD., pp. 58–65.
Article entitled: "Evidenced–Based Natural Medicine, A Review of the Effectiveness of *Cimicifuga racemosa* (Black Cohosh) for the Symptoms of Menopause", Shari Lieberman, PhD., C.N.S., Journal of Womens Health, vol. 7, No. 5, 1998, Mary Ann Liebert, Inc., University of Bridgeport, Bridgeport, Connecticut.
Article entitled "Menopause without Medicine", 3rd Edition (1995), Chapter 3: Hot Flashes; Linda Ojeda, PhD., Hunter House, Alameda Calif.
Article entitled "Menopausal Symptoms", www.thorne.com, Sep. 9, 1999.
Article entitled Black Cohosh, "Menopausal Years: Alternative Approaches for Women 30–90", Susan S. Weed, Ash Tree Publishing, 1992.

\* cited by examiner

*Primary Examiner*—Herbert J. Lilling

(57) ABSTRACT

An herbal composition is disclosed and claimed. One of the compositions disclosed includes the combination of sage leaf, red raspberry leaf, bayberry bark, capsicum pepper, damiana leaf, ginger root, licorice root, vaierian root, black cohosh root, red clover extract and kudzu root. Other compositions of the herbs are disclosed and claimed. The composition is bound in tablet form and administered orally. Alternatively, the composition is applied to the skin of the user as a cream, a patch or spray.

5 Claims, No Drawings

HERBAL COMPOSITION

FIELD OF THE INVENTION

The invention is an herbal composition for women for the treatment of premenstrual syndrome, perimenopausal symptoms, menopausal symptoms and postmenopausal symptoms.

BACKGROUND OF THE INVENTION

Menopause is defined as the cessation of menstruation in women. Six to twelve months without a period is the commonly accepted rule for diagnosing menopause. The follicle stimulating hormone ("FSH") laboratory test is used by physicians in diagnosing menopause. Most women experience menopause between the ages of 40 and 55. Menopause is characterized by hot flashes, headaches, night sweats, atrophic vaginitis, frequent urinary tract infections, cold hands and feet, forgetfulness and an inability to concentrate. Emotional indicators of menopause include distress, irritability, mood swings, depression and decreased sex drive. There are many undesirable symptoms too numerous to articulate which are attributed to pre-menstrual, perimenstrual and premenopause changes in the female body.

Hot flashes are common in menopausal women. Dilation of peripheral blood vessels leads to a rise in skin temperature and flushing of the skin. The skin of a menopausal women during a hot flash becomes red and warm for a period of a few seconds up to two minutes. During a hot flash, the skin on the head and neck of a menopausal woman is particularly affected and becomes red and warm. Other symptoms such as increased heart rate, headaches, dizziness, weight gain, fatigue and insomnia may be associated with a hot flash. Sixty-five (65) to eighty (80) percent of the menopausal women in the United States experience hot flashes. Hot flashes may appear prior to the cessation of the menses and may be the first sign that menopause is approaching.

The term "perimenopausal" is the time period prior to menopause and the term "postmenopausal" is the time period after menopause.

Menopause is now viewed as a disease rather than a normal physiological process. Current medical treatment of menopause involves the use of hormone replacement therapy ("HRT") for an indefinite period of time utilizing a combination of estrogen and progesterone. Estrogen is one of a group of steroid hormones including estriol, estrone and estradiol that controls the amount of sexual development promoting the growth and function of the female sex organs and female secondary sexual characteristics. Synthetic hormones are made in an attempt to mimic the action of naturally occurring hormones.

Progesterone is a steroid hormone responsible for the changes in the endometrium in the second half of the menstrual cycle preparatory for implantation, development of maternal placenta and development of mammary glands. HRT is not recommended for women with hypertension, diabetes, significant liver or gallbladder disease, coronary artery disease or during pregnancy.

Beginning in the 1940's estrogen was widely prescribed for ameliorating the symptoms of menopause and over time estrogen became the medical treatment of choice for women in menopause. It is now well established that estrogen replacement therapy is associated with a an increased risk of developing uterine cancer, breast and ovarian cancer. Estrogen has also been discovered to cause heart attack and strokes. Estrogen was prescribed for women in an attempt to compensate for the normal decline in estrogen that comes with age.

In an effort to reduce the increased risk of cancer which was being observed through the use of estrogen, physicians and drug companies began recommending that estrogen be combined with progesterone. The combination of estrogen and progesterone has reduced the risks of certain types of cancer such as endometrial cancer but other cancers occur through the use of this combination. Hypertension and coronary artery disease are additional undesirable side effects which occur in women treated with estrogen and progesterone. Women and their physicians are naturally concerned about these remaining risks.

Certain herbs are recognized in the treatment of hot flashes. They include but are not limited to licorice root (*Glycyrrhiza glabra*), chaste berry (*Vitex agnus-castus*), black cohosh (*Cimicifuga racemosa*) and angelica (*Cong quai*(*angelica sinensis*). The literature states that these herbs may be effective individually and that combining them is thought to produce an even greater benefit. Black cohosh relieves hot flashes, depression and vaginal atrophy.

Phytoestrogens and phytoprogesterone are plant compounds which closely resemble estrogen and progesterone. Phytohormones are capable of binding to estrogen and progesterone receptors. Phytoestrogens represent a family of plant compounds that have been shown to have both estrogenic and antiestrogenic properties. If estrogen levels are low, phytoestrogens will cause an increase in estrogen effect since they have some estrogenic activity. If estrogen levels are high, phytoestrogens will cause a decrease in estrogen since they bind to estrogen-receptor sites. Some foods such as soy, nuts, whole grains, clover and apples contain phytoestrogens. Women in some cultures remote to the United States have a largely plant based diet and do not experience the symptoms previously mentioned herein and/or do not experience them to the extent that women in the United States experience them. Diets high in phytoestrogens are believed to explain why the women in these remote cultures do not experience the menopausal symptoms that women here in the United States experience. Japanese women intake considerably more phytoestrogens than do American women.

Isoflavones are structurally similar to the body's natural form of estrogen and are found in soy. Isoflavones are a form of phytoestrogens. Isoflavones when consumed by a menopausal woman have many cardiovascular benefits. The estrogen like activity of isoflavones can reduce hot flashes and night sweats.

U.S. Pat. No. 5,707,630 to Morrow issued Jan. 13, 1998 is directed to an herbal compound for women suffering from premenstrual syndrome but it does not disclose or claim the subject matter of the instant application and invention. U.S. Pat. No. 6,238,707 to Chun issued May 29, 2001 is directed to a hormone balance composition but it does not disclose or claim the subject matter of the instant application and invention. U.S. Pat. No. 5,569,459 to Shlyankevich issued Oct. 29, 1996 is directed to a pharmaceutical compositions for the management of premenstrual syndrome and alleviation of menopausal disorders but it does not disclose or claim the subject matter or the instant invention. In fact, the '459 patent states that most of the plant products identified therein and some vitamins and minerals are used in different special menopausal formulas which are manufactured by several producers and are available in health food stores.

Further, the '459 patent states that none of these products has proved satisfactory in the treatment of post-menopausal disorders and that all of the known products merely treat symptoms and do not alleviate a hormonal deficiency.

The invention will be better understood when reference is made to the following Summary Of The Invention, Description Of The Invention and Claims which follow hereinbelow.

SUMMARY OF THE INVENTION

It is an object of the present invention to provide an herbal composition which treats premenstrual, perimenopausal, menopausal, and postmenopausal symptoms.

It is a further object of the present invention to provide an herbal composition which provides relief from the distress and discomfort of the premenstrual symptom through the stages of menopause.

It is a further object of the present invention to provide an herbal composition which stimulates naturally occurring hormones so as to minimize or eliminate the symptoms or effects of premenstrual syndrome, perimenopause, menopause and postmenopause.

The invention disclosed and claimed includes sage leaf, red clover extract and kudzu root extract used by themselves. Sage leaf and red clover extract may be used by themselves without the kudzu root extract. Sage leaf and kudzu root extract may be used by themselves without the red clover extract.

Sage leaf, red clover extract, and black cohosh root may be used by themselves. Sage leaf, red clover extract and licorice may used by themselves. Sage leaf, damiana leaf, black cohosh root and red clover extract by themselves.

One herbal composition comprises 200 milligrams (mg) of sage leaf, 36 mg of red raspberry leaf, 18 mg of bayberry bark, 18 mg of capsicum pepper, 18 mg of damiana leaf, 18 mg of ginger root, 18 mg of valerian root, 18 mg of licorice root, 14 mg of black cohosh, 10 mg of red clover extract and 10 mg of kudzu root extract. Preferably the composition is in tablet format with the binder used in equal proportion (by weight) to the herbs (i.e., the active ingredients). Different compositions of the tablet are specifically contemplated. For instance, differing amounts of the sage leaf may be used as desired.

The invention will be better understood when reference is made to the following description of the invention and claims which follow hereinbelow.

DESCRIPTION OF THE INVENTION

Sage Leaf: (*Salviae folium*) Therapeutic action: Antibacterial, Fungistatic, Virustatic, Astringent, Secretion-promoting, Perspiration-inhibiting. Contains plant estrogens. This herb has many medical properties and is especially good for hot flashes and reducing excessive sweating. As used herein and in the claims sage is synonymous with sage leaf.

Red Raspberry Leaf: (*Rubus idaeus*) Therapeutic action: Astringent, nutritive, diuretic, stimulant and tonic. This is an estrogenic herb and has a direct action on the muscles of the uterus helping to tone weakened uterine muscles and relaxing uterine and intestinal spasms. Can also assist in correcting a prolapse of the uterus and vagina. This herb is also used for disorders of the gastrointestinal tract, the respiratory tract and the cardiovascular system. Helpful in purifying the skin and blood. As used herein and in the claims red raspberry is synonymous with red raspberry leaf.

Bayberry Bark (*Myrica cerifera*) Therapeutic action: Astringent, tonic, stimulant, aromatic. Boosts vitality and resistance and has a general good effect on the reproductive system. Synergistically works well with capsicum, ginger and sage.

Capsicum Pepper (*Capsicum frutescent*) Therapeutic action: Stimulant, antiseptic, tonic, calmative, analgesic, digestive, detoxifying. Good for circulation and relieving muscle tension and spasm, warding off winter blues, lethargy and chills. Rejuvenating. The warming effect relieves spasms and pain due to poor circulation of and around the reproductive organs.

Damiana Leaf: (*Turnera diffusa*) Therapeutic action: Aphrodisiac, nervine, adapogenic, alterative. This herb is a pituitary regulator and anti depressant. It is also an aphrodisiac and is of benefit for sexual difficulties. Strengthening and stimulating during exertion in addition to boosting and maintaining mental and physical capacity. As used herein and in the claims damiana is synonymous with damiana leaf Ginger Root: (*Zingiber officinalis*) Therapeutic action: Antispasmodic, anti-inflammatory, circulatory stimulant, antiemetic, carminative. Ginger is inotropic (promoting heart muscle tone). Good for nausea and aids in digestion. As used herein and in the claims ginger is synonymous with ginger root.

Licorice Root: (*Liquirtiae radix*) Therapeutic action: Stimulant, expectorant, antispasmodic. Licorice has an estrogenic effect. This herb will stimulate your adrenals and contains several flavonoids of flavanone and isoflavanone derivatives in addition to the potassium and calcium salts of the glycyrrhizic acid. It also contains phytosterols and coumarins. Also has a good effect on the upper respiratory tract. As used herein and in the claims licorice is synonymous with licorice root.

Valerian Root: (*Valeriana officinalis*) Therapeutic action: Nervine, sedative, antispasmodic. Valerian is used for restlessness, insomnia, mental strain, lack of concentration, excitability, stress, headache, nervous cardiopathy, menstrual agitation, nervous stomach, cramps and uterine spasms. As used herein and in the claims valerian is synonymous with valerian root.

Black Cohosh Root: (*Cimicifugae racemosae*) Therapeutic action: Alterative, antispasmodic, nervine. This herb is known for its plant-based hormones and their positive effects on hot flashes, night sweats, headaches, heart palpitations, depression and anxiety associated with menopause, mood changes and drying and thinning of the vagina. Also contains salicylates, a component of aspirin. As used herein and in the claims black cohosh is synonymous with black cohosh root. Black cohosh has an estrogen-like action and is believed to be a progesterone precursor. Black cohosh root is considered phytoestrogens.

Red Clover Extract: (*Trifolium partense*) Therapeutic action: Alternative, stimulant, antispasmodic. Contains plant estrogens called coumestrol and one of its medical actions is to stimulate the ovaries and is used specifically for treatment of ovarian cysts. It is alkalinizing, restoring healthy body function. Used to relieve hot flashes. Vascular reactivity may be improved by supplementation with isoflavones isolated from Red Clover. Isoflavones from red clover improve systemic arterial compliance. As used herein and in the claims red clover is synonymous with red clover extract.

Kudzu Root Extract: (*Pueraria lobata*) Therapeutic action: Stimulant. An excellent source for both genistein and daidzein. It is one of the earliest medical plants used in traditional Chinese medicine. This root has many profound pharmacological actions including antidipsotropic activity (anti-alcohol abuse). As used herein and in the claims kudzu is synonymous with kudzu root extract.

The invention disclosed and claimed includes sage leaf in the range of 25 milligrams (mg) to 350 mg, red clover extract in the range of 10 mg to 500 mg and kudzu root extract in the range of 10 to 250 mg used by themselves. Sage leaf in the range of 25 mg to 350 mg and red clover extract in the range of 10 mg to 500 mg may be used by themselves without the kudzu root extract. Sage leaf in the range of 25 mg to 350 mg and kudzu root extract in the range of 10 to 250 mg may be used by themselves without the redclover extract.

Sage leaf in the range of 25 mg to 350 mg, red clover extract in the range 10 mg to 500 mg, and black cohosh root in the range 10 mg to 250 mg may be used by themselves. Sage leaf in the range of 25 mg to 350 mg, red clover extract in the range of 10 mg to 500 mg and licorice in the range of 10 mg to 300 mg may used by themselves. Sage leaf in the range of 25 mg to 350 mg, damiana leaf in the range of 15 mg to 500 mg, black cohosh root in the range of 10 to 250 mg and red clover extract in the range of 10 mg to 500 mg.

One herbal composition (by weight) comprises 200 milligrams (mg) of sage leaf, 36 mg of red raspberry leaf, 18 mg of bayberry bark, 18 mg of capsicum pepper, 18 mg of damiana leaf, 18 mg of ginger root, 18 mg of valerian root, 18 mg of licorice root, 14 mg of black cohosh, 10 mg of red clover extract and 10 mg of kudzu root extract. Initial studies of this composition are in progress and good results have been obtained for treatment of many of the symptoms associated with menopause. Preferably the composition is in tablet format with the binder used in equal proportion by weight to the herbs (i.e., the active ingredients). For a given weight of active ingredients (i.e., the herbs) and equal weight of binder is used.

Another herbal composition (by weight) comprises 25 to 350 milligrams (mg) of sage leaf, 20 to 350 mg of red raspberry leaf, 10 to 250 mg of bayberry bark, 10 to 200 mg of capsicum pepper, 15 to 500 mg of damiana leaf, 10 to 250 mg of ginger root, 10 to 200 mg of valerian root, 10 to 300 mg of licorice root, 10 to 250 mg of black cohosh, 10 to 500 mg of red clover extract and 10 to 250 mg of kudzu root extract.

Different compositions of the tablet are specifically contemplated. For instance, differing amounts of the sage leaf may be used as desired. Further, different relative proportions by weight of the binders may be used. Different binders having a different composition may be used.

Typically the binder comprises dicalcium phosphate, microcrystalline cellulose, croscarmellose sodium, stearic acid, silica, magnesium stearate and a cellulose fiber coating. Other binders employing only some of the aforementioned ingredients are contemplated. Use of high quality herbal products in the composition is suggested in combination with a coated tablet so as to enable and facilitate digestion on an empty stomach. The tablets may be coated with a food glaze. The tablets are taken orally.

It is specifically contemplated that the compositions claimed and described herein may be administered through patches affixed to the body of the user. Further, the compositions claimed herein may be carried by a cream which is applied to the skin of the user. Sprays including oral sprays may be used. The herbal composition or part thereof is absorbed through the skin of the user.

The herbs are typically supplied in barrels or other large quantities. The herbs are then tested for quality purposes. Next, the herbs are ground, measured out by weight, and then mixed with a binder. A mixer capable of mixing the ground herbs is used. Processing is done in a sterile environment. Once mixed, the material is fed through a pill press.

The foregoing description has been set forth by way of example only and is not intended to be a limitation on the claims which follow hereinbelow. For instance, the proportion of ingredients relative to each other may be changed without departing from the spirit and scope of the appended claims.

I claim:

1. An herbal composition comprising 200 milligrams (mg) of sage leaf, 36 mg of red raspberry leaf, 18 mg of bayberry bark, 18 mg of capsicum pepper, 18 mg of damiana leaf, 18 mg of ginger root, 18 mg of valerian root, 18 mg of licorice root, 14 mg of black cohosh, 10 mg of red clover extract and 10 mg of kudzu root extract.

2. An herbal composition, by weight, comprising 25 to 350 milligrams (mg) of sage leaf, 20 to 350 mg of red raspberry leaf, 10 to 250 mg of bayberry bark, 10 to 200 mg of capsicum pepper, 15 to 500 mg of damiana leaf, 10 to 250 mg of ginger root, 10 to 200 mg of valerian root, 10 to 300 mg of licorice root, 10 to 250 mg of black cohosh, 10 to 500 mg of red clover extract and 10 to 250 mg of kudzu root extract.

3. An herbal composition as claimed in claim 2 in combination with a carrier selected from the group of a patch, a cream or a spray.

4. An herbal composition comprising sage leaf, red raspberry leaf, bayberry bark, capsicum pepper, damiana leaf, ginger root, valerian root, licorice root, black cohosh, red clover extract and kudzu root extract.

5. An herbal composition as claimed in claim 4 in combination with a carrier selected from the group of a patch, a cream or a spray.

* * * * *